United States Patent [19]

Muckerheide

[11] 4,120,293
[45] Oct. 17, 1978

[54] LASER SYSTEM AND METHOD

[75] Inventor: Myron C. Muckerheide, Schofield, Wis.

[73] Assignee: A. Ward Ford Memorial Institute, Inc., Wausau, Wis.

[21] Appl. No.: 724,119

[22] Filed: Sep. 17, 1976

[51] Int. Cl.² .............................................. A61B 6/00
[52] U.S. Cl. .................................... 128/2 A; 128/395; 330/4.3
[58] Field of Search ........................ 128/2 A, 2 R, 4, 6, 128/303.1, 362, 395–398; 219/121 L, 121 LM; 250/272–274, 302, 307; 330/4.3; 332/7.5; 350/96 WG

[56] References Cited

U.S. PATENT DOCUMENTS

| | | | |
|---|---|---|---|
| 3,467,098 | 9/1969 | Ayres | 128/395 X |
| 3,471,215 | 10/1969 | Snitzer | 128/398 X |
| 3,659,613 | 5/1972 | Bredemeier | 128/395 |
| 3,777,742 | 12/1973 | Aumiller et al. | 128/2 A |
| 3,834,391 | 9/1974 | Block | 128/398 X |
| 3,974,454 | 8/1976 | Sturel | 330/4.3 |

FOREIGN PATENT DOCUMENTS 1,252,732  11/1971  United Kingdom .............. 350/96 WG

OTHER PUBLICATIONS

Dulberger et al., "Electronics" Nov. 24, 1961, pp. 54–57.

Primary Examiner—William E. Kamm
Attorney, Agent, or Firm—Andrus, Sceales, Starke & Sawall

[57] ABSTRACT

A laser system employs a laser amplifier doped with Neodymium ions having a planar input surface receiving a laser beam having a wavelength of 1.06 microns from a laser generator also employing a Neodymium doped crystal. The laser amplifier provides an output face axially aligned with the input face and having a diameter of approximately one-fifth of the input face diameter. Approximately 88 percent of the axial length of the amplifier crystal is tapered to provide a continuously decreasing cross-section from a point near the input face to a point near the output face and forming a tapered spontaneous pumping zone of substantially reduced diameter adjacent the output face. A special retainer encloses the laser amplifier which direct output pulses from the output face through a bronchoscope to vaporize carbon and possibly other particles located on alveoli within a lung of a living mammal. X-ray producing particles may be introduced to the alveoli for subsequent vaporization by the amplified laser beam which is sensed to provide an output for diagnosis purposes.

10 Claims, 8 Drawing Figures

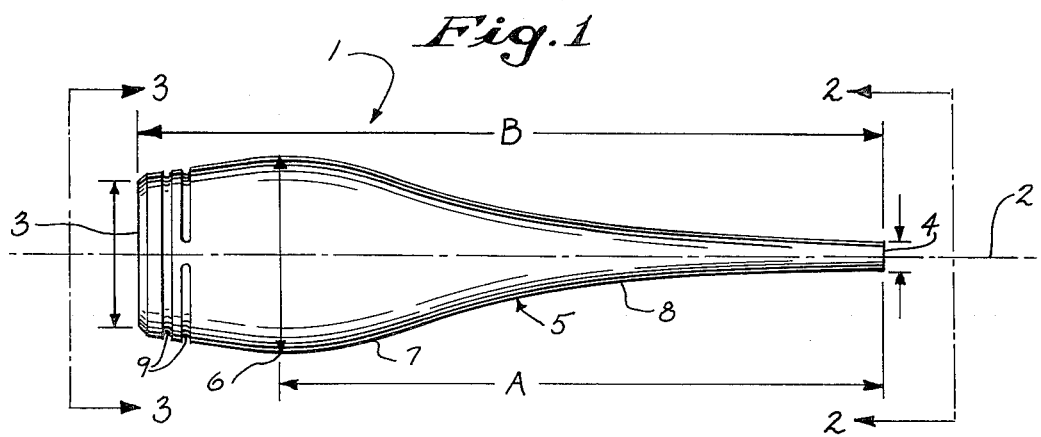
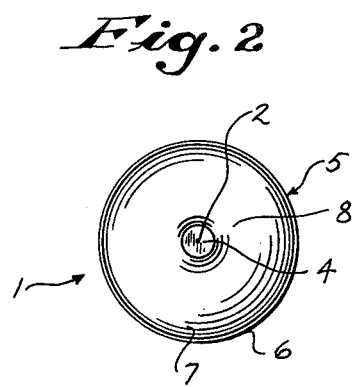
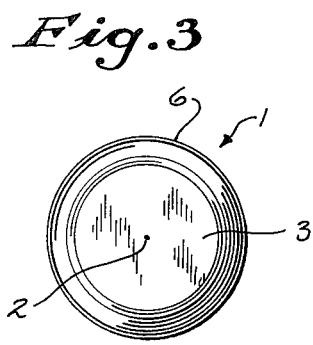
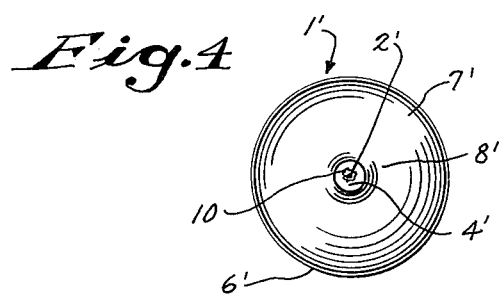
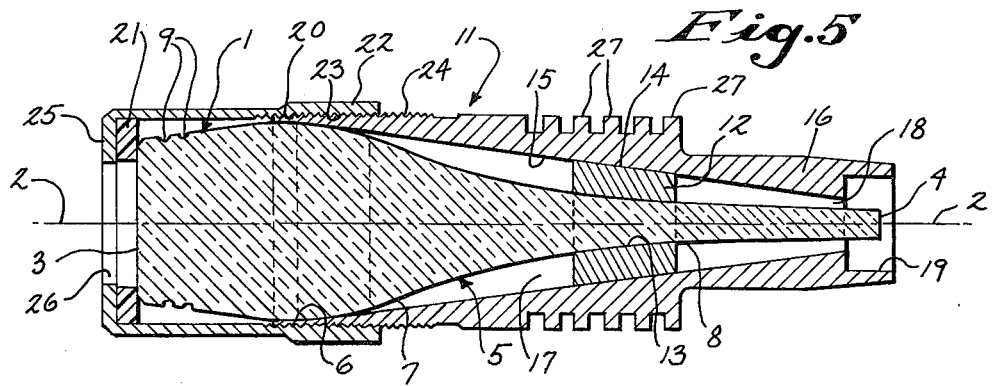

LASER SYSTEM AND METHOD

BACKGROUND OF THE INVENTION

This invention relates to a laser system and method of vaporizing absorbing material located at inaccessible areas.

Light conducting fibers and/or focusing lenses have been employed in laser applications for surgery and industry applications or the like. Some laser systems employ an auxiliary laser generator which either by itself or in combination with a main laser generator forms a laser resonating cavity through the use of mirrors or the like, such as shown in U.S. Pat. Nos. 3,821,510 and 3,622,743. Other systems employ various light conduits or the like which conduct laser beams through a torturous path by employing flexible conduits or flexible light pipes, such as shown in U.S. Pat. Nos. 3,843,865 and 3,467,098.

SUMMARY OF THE INVENTION

This invention relates to a laser system and method of diagnosing a condition at an inaccessible area.

In one aspect of the invention, a system selectively conducts a laser beam to vaporize absorbing material located at an internal area of a living mammal. In such system, a laser generator selectively supplies a laser beam having a predetermined wavelength to an input face of a laser amplifier. An output face of the amplifier provides a cross-sectional dimension which is less than one-half of the input face cross-sectional dimension. The amplifier is constructed to provide a cross-sectional dimension which continuously decreases from a point adjacent to the input face to a point adjacent the output face. Such construction provides a tapered spontaneous pumping zone of substantially reduced cross-section which is adjacent to the output face. Such laser amplifier selectively emits a laser beam having the predetermined wavelength from the output face to the internal area and vaporize the absorbing material in response to a received laser beam from the generator.

A unique laser amplifier is thus provided for use with a laser generator and includes a crystal doped with ions having characteristics similar to the characteristics employed in the laser generator. The laser amplifier crystal provides an outer substantially circular surface defining a central axis with the radius continually varying along the axis of the crystal. The amplifier selectively receives the laser input of the input face or surface for pumping the crystal thereby causing population inversion. The amplifier crystal output face or surface is axially spaced from the input face by a predetermined axial length with the output surface selectively emitting an amplified laser output in response to a received laser input when pumped to a predetermined level. The diameter or cross-sectional dimension of the crystal continuously decreases over at least 50 percent of the axial length to provide the tapered spontaneous pumping zone.

In a preferred construction, the input and output faces of the laser amplifier are substantially parallel planar surfaces spaced along the axis of the amplifier. The amplifier provides a substantially circumferential outer surface about such axis which has a diameter varying along a substantial portion of the axial length of the amplifier. In an alternate configuration, a mask is associated with the output planar face to effect a controlled pattern output of the amplified laser beam. Such a mask may include voids or deviations in the output planar face.

The laser amplifier is removably retained and enclosed by a specially constructed apparatus including an annular shaped casing with a cone shaped opening having good reflective properties. A first axial end of the casing circumferentially engages an outer circumferential surface of the amplifier at an axially spaced distance from the input face and a second axial end provides a circular opening with a diameter greater than the diameter of the output face. A spacing ring provides a cone shaped outer surface which engages the inner surface of the cone shaped opening. The spacing ring further provides a tapered opening having an inner surface which engages a tapered outer surface of the amplifier. A cap provides internal threads which removably engage exterior threads of the casing at the first axial end and further provides an end wall which removably applies pressure to the input face of the amplifier through a spacing washer. Both the end wall of the cap and the washer provide aligned circular openings which permit the selective passage of laser pulses from the laser generator to the input face.

Conduit means is employed between the amplifier output face and the absorbing material to permit the passage of the amplifier laser beam to the absorbing material. In one mode of operation, an amplified laser beam having a wavelength of 1.06 microns is passed through a bronchoscope opening to vaporize carbon located an alveolus of a lung of a living mammal.

In another aspect, a particle propelling apparatus is connected with the conduit means to propel selected particles through the conduit passage and onto the absorbing material. A sensing apparatus responds to the vaporization of such particles and the absorbing material to provide an output indicative of the status of the absorbing material. In one form of the invention, an insufflator selectively forces stored particles by the use of compressed gas or the like onto the absorbing material by passing through the conduit means. Sensing of the vaporization of the added particles and absorbing material, such as carbon located within the lungs for example, is accomplished through an optical circuit coupled to a spectrograph which provides an output responsive to the sensed vaporization for diagnosis and treatment in response to the supply of the amplified laser beam through the conduit opening.

In another aspect of the invention, a system is provided which selectively conducts a laser beam to vaporize absorbing material located at an internal area of a living mammal where X-ray producing particles are also vaporized. Such particles are inserted into the internal area so as to be adjacent to the absorbing material. A laser beam is thereafter directed to the internal area to vaporize both the particles and absorbing material.

The invention thus provides a desirable laser system and method which can be utilized for a wide variety of applications including the diagnosis of and/or removal of carbon from the alveoli within the lung of a living mammal.

BRIEF DESCRIPTION OF THE DRAWINGS

The drawings furnished herewith illustrate the best mode presently contemplated by the inventor and clearly disclose the above advantages and features as well as others which will be readily understood from the detailed description thereof.

In the drawings:

FIG. 1 is a side elevational view of a laser amplifier employing a crystal doped with Neodymium ions;

FIG. 2 is an axial end view taken at 2—2 of FIG. 1;

FIG. 3 is an axial end view opposite to the view of FIG. 2 and taken at 3—3 in FIG. 1;

FIG. 4 is an alternative embodiment showing an axial end view of an alternative embodiment of a laser amplifier which is similar to the end view of FIG. 2;

FIG. 5 is a sectional view showing the laser amplifier of FIG. 1 retained by a releasable container;

DESCRIPTION OF THE PREFERRED ILLUSTRATED EMBODIMENT

Figure 6:
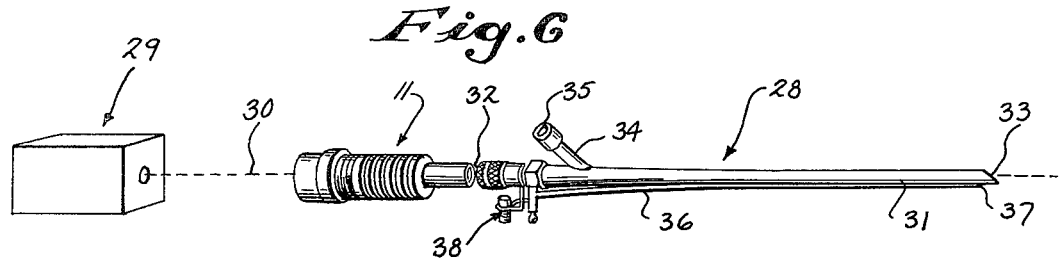
FIG. 6 is a perspective view showing the container of FIG. 5 functioning with a laser source and a bronchoscope and illustrating the application of an amplifier laser beam to a lung for medical purposes.

FIG. 1 illustrates a laser amplifier 1 which is formed from Crown-Barium glass which has been doped with Neodymium ions through the adding of approximately 5 percent $Nd_2O_3$ (by weight). The laser amplifier 1 is formed along and about an axis 2 and includes a circular shaped planar input face or surface 3 and an axially spaced planar output face or surface 4. The diameter of the input face 3 is more than twice the dimension of the output face 4. As an example of one preferred embodiment, the diameter of the output face 4 may constitute approximately 5 millimeters while the diameter of the input face 3 may constitute approximately 25 millimeters.

The laser amplifier 1 provides a circumferential outer surface 5 which varies in diameter along the axial length of amplifier 1. As an example of one preferred embodiment of the invention, the diameter near the input face 3 increases gradually such as from 25 millimeters at face 3 to a maximum diameter at 6 which may constitute approximately 33 millimeters, for example. The circumferentially shaped outer surface 5 gradually decreases in cross-sectional area from a location at 6 which is adjacent input face 3 to the output face 4, which may constitute 5 millimeters for example. The axial distance A from the maximum diameter point 6 to the output face 4 may, in one form of the invention, constitute approximately 114 millimeters whereas the overall axial length B between the input and output faces 3 and 4 may constitute approximately 129 millimeters. In such a configuration as described with respect to one form of the preferred embodiment, the cross-sectional diameter increases by approximately 32 percent from the input face 3 to the point of maximum diameter at 6 and thereafter decreases by approximately 85 percent to the output face 4. It is thus noted that the diameter continuously decreases over approximately 88 percent of the axial length.

As illustrated in FIG. 1, the axially extending outer surface provides a convex configuration at 7 and a concave configuration at 8. A series of axially spaced circumferential grooves 9 are located adjacent the input face 3 and are employed for grasping the amplifier 1 during the fabrication of the outer surface thereof.

FIG. 4 represents an end view of an alternative embodiment of an amplifying laser similar to the amplifier shown in FIGS. 1–3 and identical numbers primed will be employed to show substantially similar or identical features. The alternative construction in FIG. 4 shows a mask 10 formed on or in the planar output face 4'. In a preferred construction, the mask 10 is formed by a cut or indentation which protrudes into the amplifier laser for a short distance, such as a fraction of a millimeter, for example. One method of forming the mask 10 may include the direction of a high intensity laser beam directly along the axis 2' of the amplifying laser 1' so as to burn or otherwise form the hole or indentation in the output planar face 4' as illustrated at 10.

FIG. 5 illustrates the placement of the amplifying laser 1 within a casing or support 11. An annular retaining ring 12 has a central tapered opening 13 which firmly engages the outer surface 8 of the laser amplifier 1. An outer circumferential, axially tapered surface 14 of ring 12 engages an axially tapered, circumferential internal surface 15 of a housing or casing 16. The internal surface 15 of casing 16 forms a cone shaped opening 17 which has an axial end 18 terminating at a circular opening 19 having a diameter greater than the diameter of opening 18. An axial end 20 of casing 16 directly engages the surface portion 6 of the amplifying laser 1. A resilient annular washer or spacer 21 seats against the radially spaced edges of the input planar surface 3 while a retaining cap 22 provides internal threads 23 which selectively engage a series of external threads 24 formed on the exterior portion 20 of casing 16. The cap 22 includes an end member 25 which engages the ring 21 thereby retaining the amplifier laser 1 in a secured retained position within the casing 16. The end portion 25 of cap 22 includes a circular opening 26 which permits the entry of laser beams from an external source to impinge upon the exposed planar input surface 3 of amplifier laser 1. In a similar manner, the circular opening 19 permits the exit of laser beams from the exposed planar surface 4. A plurality of spaced ridges or projections 27 are formed upon the exterior surface of casing 16 and permits fluid cooling of the assembly 11. In addition, it may be desirable to conduct a coolant through the cone shaped opening 17 through entrance and exit ports (not shown).

FIG. 6 illustrates the employment of the assembly 11 which retains the laser amplifier 1 in conjunction with a bronchoscope 28 and a laser source 29. The source 29 may constitute any commercially available laser beam generating apparatus capable of continuous or pulsed laser outputs. For example, the source 29 could provide a laser beam output as illustrated at 30 constituting a substantially long pulse (such as 10 microseconds, for example) of 2 to 10 joules having a wavelength of 1.06 microns and issuing from an $Nd^{+3}$ glass laser which has been doped with Neodymium ions, for example. Alternatively, the invention could be employed with a continuous beam or with short pulses occurring for a few nanoseconds, for example.

The bronchoscope 28 as illustrated is a conventional medical instrument including an elongated tube 31 having a central opening (not shown) which permits the passage of light, fluids, solid particles or the like between a first opening 32 at one axial end and a second opening 33 at a second oppositely disposed axial end. An laterally protruding tube 34 provides an inner opening 35 which communicates with the central opening of tube 31. A tube 36 is shown mounted externally to tube 31 and contains an elongated glass optical fiber which extends from a sensing end 37 to an output end at 38. The optical fiber retaining tube 36 may, if desired, be mounted within the internal opening of tube 31.

Figure 7:
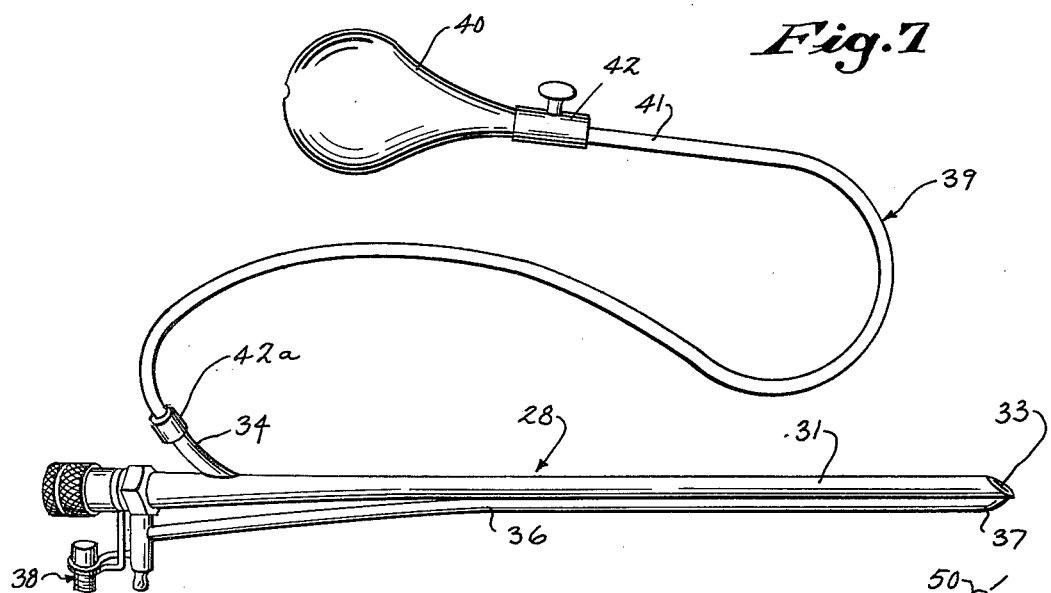
FIG. 7 is a perspective view illustrating the application of X-ray producing particles into a lung of a living mammal.

FIG. 7 illustrates the use of an insufflation apparatus 39 which includes a selectively compressible bulb 40 removably joined to a flexible tube 41 through an adjustable clamp 42. The tube 41 contains a hollow opening (not shown) which communicates with opening 35 and thus with the internal passage of tube 31. A coupling element 42a may be utilized to form a storage container for particles to be passed through tube 31.

Figure 8:
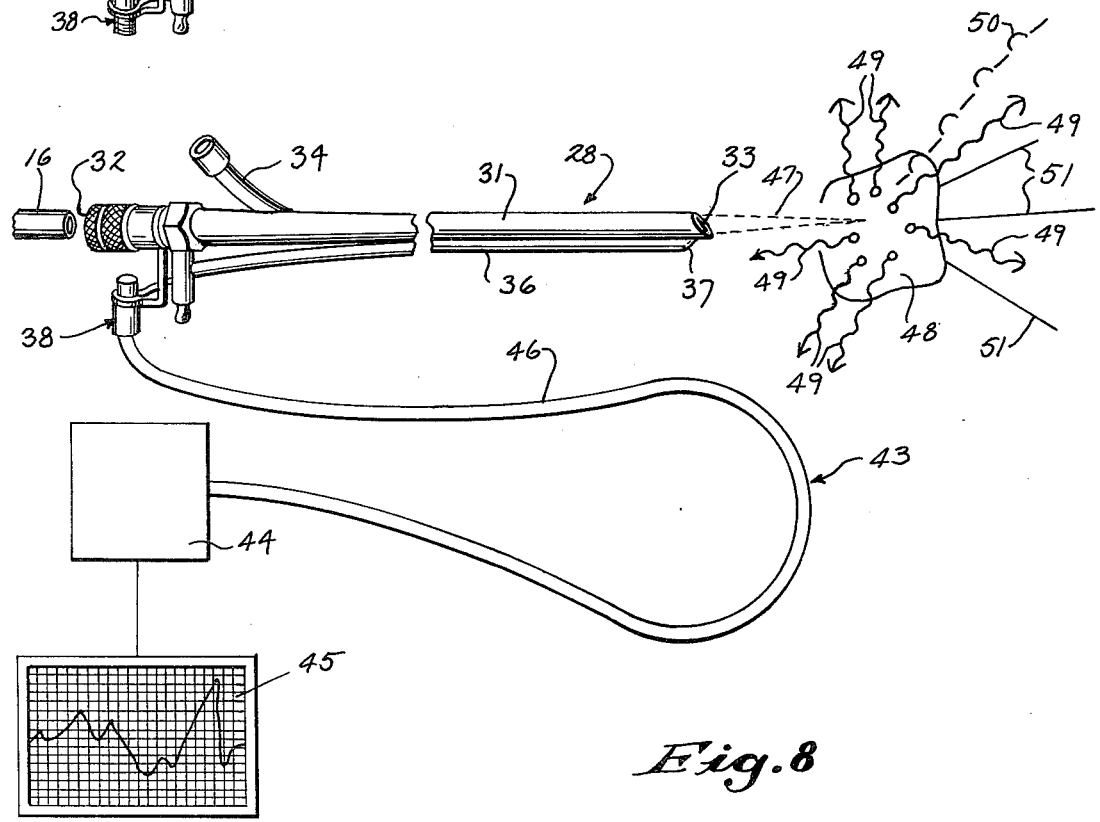
FIG. 8 is a perspective view illustrating the operation of the system shown in FIG. 6 in conjunction with a spectrograph for diagnosis.

FIG. 8 illustrates a spectrograph sensing apparatus 43 which includes a spectrograph analyzer 44 providing an output 45. An input of the sensing apparatus includes an optical fiber 46 which is removably connected to the optical fiber within tube 36 as at 38.

In operation, the outwardly extending tube 31 of bronchoscope 28 is inserted into the esophagus so that the outer opening 33 is located immediately adjacent one or more alveolus within the lung of a living mammal. The outer end 19 of the amplifying assembly 11 is located adjacent or connected to end 32 of bronchoscope 28 as illustrated in FIG. 6. The laser source 29 is activated to generate a series of laser pulses at a 1.06 micron wavelength which engage the exposed planar surface 3 of the laser amplifier 1. The series of laser pulses 30 cyclically continue to effect population inversion within the Neodymium doped crystal 1.

While it is desirable to align the pumping laser beam 30 exactly along axis 2 of the laser amplifier 1, it has been found cumbersome and inconvenient to initially establish and maintain such exact alignment. In many situations, the incoming laser beam 30 may be spaced from axis 2 or may be at a varied angle with respect to axis 2 when striking the planar input surface 3. The preferred embodiment desirably employs high Q-switching glass which has been doped with Neodymium ions which frequently results in a delayed emission of photon energy in response to stimulating energy as supplied by the incoming laser beam 30. When pumped to a sufficient energy level, the amplifier laser 1 emits an output laser pulse as illustrated at 47 in FIG. 6 in response to an input pulse 30.

Where the angle of incident of the incoming energizing laser beam 30 is at an angle with respect to the axis 2, output photons may be directed randomly in accordance with the stimulating laser beam. In such situation, it has been found that the convex surface 7 and concave surface 8 extending in the axial direction of the laser amplifier 1 produces unique reflection of randomly directed photons. Such reflection by the specially designed amplifier configuration provides spontaneous pumping for additional population inversion which occurs in a dominant manner at or near the diminishing cross-sectional area of the laser amplifier 1 towards the output surface or face 4. Such simultaneous and spontaneous pumping may further be enhanced through photon reflection by the cone shaped internal surface 15 of casing 16 which may be made from stainless steel, aluminum or other good reflecting metal. In any event, the spontaneous pumping through the reflected photons in the rapidly diminishing cross-sectional area portion of laser amplifier 1 has been found to provide a desirable operation in supplying an amplified laser beam from the output surface or face 4 which passes through the circular opening 19 at the axial end of assembly 11. It has further been found that the large diameter planar surface 3, which is more than twice the diameter of the output planar surface 4, readily permits the added spontaneous pumping by reflected photons as facilitated by the diverging side walls 7 and 8 of the laser amplifier 1.

When employed in conjunction with a bronchoscope as llustrated in FIG. 6, an output laser beam supplied through opening 19 of assembly 11 is directed through the internal opening of tube 31 and exits through opening 33 as illustrated at 47. The emitting laser beam 47 has a wavelengths of 1.06 microns and has been found to be desirable in vaporizing carbon deposits found upon the alveolus in lungs for the treatment of anthracosis or silicosis before resulting in anthracosilicosis. The invention may be employed with any one of a number of medical instruments such as the bronchoscope 28 to treat pneumoconiosis or with an esophagoscope or a colonscope or other such instruments where vaporization of foreign matter or deposits may be required. When employed to remove carbon from alveolus within the lung, the laser beam 47 desirably vaporizes the deposited carbon without harming or damaging the tissues forming the lung.

In a unique method for diagnosis of medical conditions within inaccessible locations, such as within the lung, the insufflation apparatus 39 is employed to insert small particles of material on or near the tissues located at the inaccessible location. In the illustration of FIG. 7, finely divided particles are placed at 35 and bulb 40 is squeezed to force compressed air through tube 41 thereby forcing the particles through the opening of tube 34 and through the passageway of bronchoscope 28 to the lung of the living mammal. Such particles are selected from matter which possesses good X-ray emitting characteristics when stimulated by photons, such as copper, gold, iron or aluminum particles, for example. After particles have been deposited within the lung or at other inaccessible tissue areas, as illustrated in FIGS. 7 and 8, the laser source 29 and laser amplifier apparatus 11 are activated as illustrated in FIG. 8 so that the amplified laser beam 47 is directed to the deposited particles illustrated at 48 within the lung. When the photons engage or strike the deposited matter 48, X-rays 49, ions 50 and electrons 51 are produced as diagrammatically illustrated in FIG. 8. The optical fiber located within tube 36 responds to visible light that is generated by the photon interaction illustrated in FIG. 8 to thereby activate the spectrograph analyzer 44 and provide a corresponding output 45. This where carbon is being detected within the alveoli of the lungs, a carbon line spectrum can be provided at 45 which is correlated with the location of the incident photon energy, the amount of such energy, and the pulse width of the incident amplified laser beam to formulate an indication of stages of pneumoconiosis for diagnosis purposes.

Where the alternative embodiment illustrated in FIG. 4 is utilized, the mask 10 will result in an annular shaped amplified laser beam which will vaporize carbon or other desired matter in an annular or donut-shaped area while leaving untouched the central area which corresponds to the centrally located masking 10 in the planar output surface 4 of the laser amplifier 1.

The laser amplifier 1 is shown in a preferred illustrated embodiment as a solid state material, namely Crown-Barium glass which is impregnated or doped to form an $Nd^{+3}$ glass laser. The amplifier 1 could also be fabricated so as to provide an internal cavity confirmed by the exterior shape illustrated in FIG. 1 and containing a gas or liquid commonly used in laser applications.

The laser amplifier of the invention is specially shaped with a diverging cross-sectional area to an output planar surface and provides a desirable amplified laser output without destroying the glass lattice of the $Nd^{+3}$ laser while employing a 1.06 micron laser beam. Such construction has been found to deliver a focused amount of laser radiation at a greater intensity. The extremely large diameter input planar surface permits desirable operation from various coupling angles with respect to the central axis of the laser amplifier 1. In addition, a sequence of operations is provided in which diagnosis can readily be performed of conditions at a remotely located and inaccessible location.

Various modes of carrying out the invention are contemplated as being within the scope of the following claims particularly pointing out and distinctly claiming the subject matter which is regarded as the invention.

I claim:

1. A system selectively conducting a laser beam to vaporize absorbing material located at an internal area of a living mammal, comprising a laser generator selectively supplying a laser beam having a predetermined wavelength, and a laser amplifier crystal having a beam output face spaced from a beam input face having a cross-sectional dimension which is greater than twice the cross-sectional dimension of said output face, said amplifier having a cross-sectional dimension which continuously decreases from a point adjacent said input face to a point adjacent said output face and providing a tapered spontaneous pumping zone of substantially reduced cross-section adjacent said output face and selectively emits a laser beam of said predetermined wavelength from said output face into said internal area and vaporizing said absorbing material.

2. The system of claim 1, wherein said input and output faces are substantially parallel planar surfaces spaced along an axis of said amplifier.

3. The system of claim 1, wherein said amplifier provides a substantially circumferential outer surface about said axis and having a diameter which varies along a substantial portion of the axial length of said amplifier.

4. The system of claim 1, and including means mounted adjacent to said beam output face and adjacent to said absorbing material and permitting the unobstructed passage of said laser beam from said amplifier to said absorbing material.

5. The sytem of claim 4, wherein said predetermined wavelength is 1.06 microns and said absorbing material includes carbon, and said passage means includes a bronchoscope providing an elongated tube opening having an input located adjacent said output face and an output end located adjacent an alveolus containing said carbon within a lung of a living mammal.

6. The system of claim 4, wherein said absorbing material includes carbon, and including means connected to said passage means and propelling particles through said passage means and onto said carbon located upon an alveolus within the lung of a living mammal, said selectively emitted laser beam vaporizing said particles and said absorbing material, and means responding to the vaporization of said particles and said carbon and providing an output indicative of the status of said carbon.

7. The system of claim 6, wherein said propelling means includes an insufflator including a source of said particles emitting X-rays in response to energization by a photon removably connected to said passage means and a source of selectively actuaged gas selectively propelling said particles through said passage means and onto said carbon.

8. The system of claim 6, wherein said indicating means includes a spectrograph having an optical circuit connected to said passage means and located adjacent said absorbing material and providing an output responsive to the sensed vaporization of said particles and said carbon for diagnosis and treatment in response to the supply of a laser beam through said passage means from said amplifier output face.

9. The system of claim 1, and including enclosure means removably enclosing said amplifier and providing an input access opening to said input face and an output access opening to said output face.

10. The system of claim 9, wherein said enclosure means includes an annular shaped casing with a cone shaped opening having a first axial end circumferentially engaging an outer circumferential surface of said amplifier at an axiallu spaced distance from said input face and a second axial end having a circular opening with a diameter greater than the diameter of said output face, a spacing ring having a cone shaped outer surface engaging said inner surface of said cone shaped opening and a tapered opening having an inner surface engaging a tapered outer surface of said amplifier, a spacing washer containing a circular opening removably engaging and beam input face, and a cap having internal threads removably engaging exterior threads of said casing at said first axial end and an end wall removably applying pressure to said input face through said spacing washer with said end wall and said washer having aligned circular openings permitting the selective passage of said laser pulses from said laser generator to said input face.

* * * * *